ayoutusing USreperi cruc cruc cross US005686253A

United States Patent [19]

Skold et al.

[11] Patent Number: 5,686,253
[45] Date of Patent: Nov. 11, 1997

[54] METHOD OF STABILIZING ENZYME CONJUGATES

[75] Inventors: Carl N. Skold; Margaret Henson; Thomas Michael Houts, all of Mountain View; Ian Gibbons, Portola Valley, all of Calif.

[73] Assignee: Behringwerke AG, Marburg, Germany

[21] Appl. No.: 450,744

[22] Filed: May 25, 1995

Related U.S. Application Data

[63] Continuation of Ser. No. 616,115, Nov. 20, 1990, abandoned.

[51] Int. Cl.$^6$ ................................................. G01N 33/535
[52] U.S. Cl. ........................... 435/7.9; 435/6; 435/188; 435/963; 435/975; 436/822
[58] Field of Search ......................... 435/6, 7.9, 188, 435/963, 975; 436/822

[56] References Cited

U.S. PATENT DOCUMENTS

| | | |
|---|---|---|
| 3,875,011 | 4/1975 | Rubenstein et al. . |
| 4,233,401 | 11/1980 | Yoshida et al. . |
| 4,454,226 | 6/1984 | Ali et al. . |
| 4,493,890 | 1/1985 | Morris . |
| 4,578,350 | 3/1986 | Armenta et al. . |
| 4,621,048 | 11/1986 | Ashihara et al. . |
| 4,686,181 | 8/1987 | Dona . |
| 4,782,023 | 11/1988 | Anawis et al. . |
| 4,804,625 | 2/1989 | Morrison et al. . |
| 5,053,326 | 10/1991 | Renz . |

FOREIGN PATENT DOCUMENTS

| | | |
|---|---|---|
| 0 061 071 A1 | 9/1982 | European Pat. Off. . |
| 0 298 654 A2 | 1/1989 | European Pat. Off. . |
| WO90/07714 | 7/1990 | WIPO . |

OTHER PUBLICATIONS

Shami, et al., *Trends in Biotechnology*, vol. 7(7), (Jul. 1989) pp. 186–190, "Stabilization of biologically active proteins".
Sullivan, et al., Practical Immunoassay, Chapter 3, pp. 37–69, Marcel Dekker, Inc. (Newe York, NY), 1984 "Enzyme Immunoassay".
Skold, et al., Journal of Immunology, vol. 138:10, (May 15, 1987) pp. 3408–3414, "Monoclonal antibodies to glucose–6–phosphate dehydrogenase from cyclic 1:1 compleses with G6PDH and act as regulatory subunits".
Frackelton, et al., J. Biological Chemistry, vol. 255, (1980) pp. 5286–5290, "Functional diversity of antibodies elicited by bacterial beta–D–galactosidase".
Ben–Yoseph, et al., Immunochemistry, vol. 12, (1975) pp. 221–226.
Turkova, et al., Journal of Chromatography, vol. 376 (1986) pp. 315–321, "Reversible andirreversible immobilization of carboxypeptidase Y using biospecific absorption".
Turkova, et al., Institute of Organic Chemistry and Biochemistry, Czechoslovak Academy of Sciences, Symposium on Biotechnology, Bratisiava, Czechoslovakia, (1987) pp. 245–260, "Formation of Biospecific complexes as a tool for oriented immobilization of enzymes".

*Primary Examiner*—David Saunders
*Attorney, Agent, or Firm*—Theodore J. Leitereg

[57] ABSTRACT

A method is disclosed for stabilizing a conjugate of an enzyme and a member of a specific binding pair (enzyme conjugate). The method comprises the step of combining the enzyme conjugate with an effective amount of an antibody for the enzyme where the antibody does not substantially inhibit the activity of the enzyme. The invention has application to assays for the determination of an analyte wherein enzyme conjugates are employed. The improvement comprises employing as a reagent in the assay an immune complex of an enzyme conjugate and an antibody for the enzyme where the antibody does not substantially inhibit the activity of the enzyme. Compositions comprising such an immune complex and kits comprising such an immune complex in packaged combination with other assay reagents are also disclosed.

44 Claims, No Drawings

METHOD OF STABILIZING ENZYME CONJUGATES

This is a continuation of application Ser. No. 07/616,115, filed Nov. 20, 1990 and now abandoned, the disclosure of which is incorporated herein by reference.

BACKGROUND OF THE INVENTION

1. Field of the Invention

This invention relates to the stabilization of enzymes, particularly where an enzyme is conjugated to a member of a specific binding pair (enzyme conjugate). Assays such as immunoassays and DNA probe assays have developed as an important tool in clinical diagnostics. In a typical assay a member of a specific binding pair (sbp member) such as an antibody or an antigen or a polynucleotide is conjugated with an enzyme to form an enzyme conjugate. The enzyme conjugate can be used in an assay in a great variety of protocols to detect the presence and/or amount of an analyte. The analyte can be a hapten, antigen or antibody, or polynucleotide that is found in a test sample prepared from biological specimens such as plasma, serum, spinal fluid, sputum, semen, fecal material, cervical and penile swabs, amniotic fluid, and the like.

In an immunoassay the presence and/or the amount of the analyte can be determined by measuring the formation of immune complexes between a second specific binding pair (sbp) member, such as a receptor, e.g., an antibody, for the sbp member of the enzyme conjugate. In DNA probe assays the analyte can be determined by formation of hybridized species involving the enzyme conjugate. The enzymes in the enzyme conjugate can, for example, act upon a substrate to produce a colored substance, such as a dye, which produces a colormetric change that can be determined instrumentally by measuring the absorbance of the dye solution, or in some cases, visually to provide an indication of the analyte. As mentioned above, haptens, antigens and antibodies can be detected by these immunoassay procedures, which have been given the general name enzyme immunoassay (EIA). Some assays for polynucleotides utilize an enzyme conjugated to a polynucleotide, such as a DNA probe, or to a hapten, antigen, or receptor such as an antibody.

In developing an enzyme conjugate for use as an assay reagent stability is an important consideration. An enzyme conjugate composition used in an assay is usually prepared well in advance of the time the assay procedure is performed. Storage of these enzyme conjugate compositions can lead to loss of enzyme activity over time due to the instability of the enzyme. This instability can be a significant disadvantage because shipping, distribution to customers and storage in inventory usually involves substantial time delays between enzyme conjugate preparation and use. Furthermore, the enzyme conjugates can be subjected to wide temperature variations and other conditions which promote the loss of enzyme activity. Accordingly, an enzyme conjugate composition which exhibits substantially improved stability characteristics by comparison with known compositions is a useful improvement in the assay field.

The homogeneous enzyme immunoassay (see, for example, U.S. Pat. No. 3,817,837) is extremely versatile in permitting spectrophotometric determinations. The assay employs an enzyme to which the analyte to be determined such as a drug is conjugated. An analyte analog is conjugated to an enzyme at a position where, when bound to its cognate antibody, the activity of the enzyme is substantially reduced. To the extent that the unknown sample contains the analyte, the amount of antibody available for binding to the analyte analog conjugated to the enzyme is reduced. Therefore, by analyzing for enzymatic activity, a significant increase in enzymatic activity over the enzymatic activity in the absence of the unknown indicates the presence of the analyte in the unknown.

The sensitivity of the homogeneous enzyme immunoassay in particular, and assays utilizing enzymes in general, is based to a substantial degree on the activity of the enzyme when conjugated and the degree of inhibitability when antibody is bound to the molecule conjugated to the enzyme. It is, therefore, desirable to have an enzyme which not only has a high turnover rate initially, but retains a substantial proportion of this turnover rate after conjugation and storage, and is strongly inhibited when antibody is bound to the molecule that is conjugated to the enzyme. Also, the enzyme should allow for strong specific binding of antibody to the conjugated organic compound.

2. Description of the Related Art

U.S. Pat. No. 4,233,401 describes an anti-enzyme homogeneous competitive binding assay. The assay is carried out in an aqueous buffered medium, normally at constant temperature, by combining in the assay medium the unknown sample suspected of containing the analyte, enzyme bound ligand, ligand receptor (anti-ligand), enzyme inhibitor (anti-enzyme), and enzyme substrates, and the enzymatic activity in the assay medium is determined. By comparing the observed enzymatic activity with an unknown to the enzymatic activity observed in an assay medium with a known amount of analyte, the amount of analyte can be quantitatively determined.

U.S. Pat. No. 4,493,890 describes a method for increasing the ability of apoglucose oxidase to combine with flavin adenine dinucleotide (FAD) and derivatives thereof to form active glucose oxidase by interacting apoglucose oxidase with an immunologically derived binding substance, e.g., an antibody or a fragment thereof, having a specific binding affinity for glucose oxidase.

U.S. Pat. No. 3,875,011 discloses conjugated enzyme compositions for use in homogeneous enzyme immunoassays. The enzyme of the enzyme conjugate is glucose-6-phosphate dehydrogenase (G6PDH).

U.S. Pat. No. 4,686,181 describes a specific binding assay employing anti-glucose-6-phosphate dehydrogenase (anti-G6PDH) as a label. The label is monitored by its ability to inhibit G6PDH.

U.S. Pat. No. 4,782,023 describes stabilized horseradish peroxidase conjugate compositions comprising an enzyme conjugate, a calcium salt and a polyethylene glycol.

U.S. Pat. No. 4,454,226 discusses a stable conjugate of peroxidase with an allergen, a non-immunoglobulin protein or a primary amino group containing drug and a preparation thereof using phenylisothiocyanate as a blocking agent and reduction by titration.

Skold, et al., in *J. Immunol.* (1987) 138 (10): 3408–3414 describe monoclonal antibodies to G6PDH that form cyclic 1:1 complexes with G6PDH and act as regulatory subunits. These complexes are stabilized in the presence of glucose-6-phosphate (G6P) and have greatly reduced enzyme activity. In the absence of G6P, the 1:1 complexes convert gradually to a more active multimeric form.

Stabilization of biologically active proteins such enzymes by the use of antibodies is described by Shami, et al. (1989) *Trends Biotechnol.*, 7 (7): 186–190. The use of antibody/ antigen interactions to protect or modulate biological activity is disclosed in European Patent Application 0 298 654.

As described above, enzymes have also been stabilized by adding inhibitors, enzyme substrates or products, or coenzymes.

SUMMARY OF THE INVENTION

One aspect of the invention concerns a method for stabilizing a conjugate of an enzyme and a member of a specific binding pair (enzyme conjugate). The method comprises the step of combining the enzyme conjugate with an effective amount of an antibody for the enzyme wherein the antibody does not substantially inhibit the activity of the enzyme.

Another aspect of the invention involves an improvement in an assay for an analyte wherein the assay comprises the steps of (a) combining a medium suspected of containing the analyte or an agent probative of the analyte with a reagent that is a conjugate of an enzyme and a first member of a specific binding pair and (b) determining the enzyme activity of the enzyme by use of a second sbp member capable of binding to the first sbp member and a substrate for the enzyme as an indication of the presence or amount of the analyte. The improvement comprises employing as the reagent an immune complex of the conjugate and an antibody for the enzyme where the antibody does not substantially inhibit the activity of the enzyme.

In another embodiment of the invention an analyte is determined by a method comprising the steps of (a) providing in combination (1) a medium suspected of containing the analyte, (2) a conjugate, comprising an enzyme and an analyte analog, bound to an antibody for the enzyme which does not substantially inhibit the activity of the enzyme, (3) an antibody for the analyte which binds to the conjugate and changes, i.e., inhibits or enhances, the activity of the enzyme and (b) determining the enzyme activity of the enzyme.

Another aspect of the invention concerns a composition comprising an immune complex comprised of (1) a conjugate of an enzyme and a member of a specific binding pair and (2) an antibody for the enzyme where the antibody does not substantially inhibit the enzyme. The composition can further include a second member of a specific binding pair where the second member is usually capable of binding the member of the conjugate.

Another aspect of the invention involves a kit comprising in packaged combination (a) an immune complex comprised of (1) a conjugate of an enzyme and a member of a specific binding pair and (2) an antibody for the enzyme where the antibody does not substantially inhibit the activity of the enzyme and (b) a substrate for the enzyme. The kit can also include other assay reagents.

DESCRIPTION OF THE SPECIFIC EMBODIMENTS

Antibodies to enzymes, which do not substantially inhibit the enzyme, stabilize enzyme conjugates without impairing their utility in enzyme assays. Enhanced stability of the enzyme in the enzyme conjugate permits a more accurate determination of the particular analyte under examination. The stabilization can be achieved while retaining the ability to alter the activity of the enzyme in the conjugate by binding of an sbp member complementary to the sbp member of the conjugate.

Before proceeding further with the description of specific embodiments of the present invention, a number of terms will be defined.

Analyte—the compound or composition to be detected. The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids: quinoline alkaloids, which include quinine and quinidine; diterpene alkaloids, their derivatives and metabolites.

The next group of drugs includes steroids, which includes the estrogens, estogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 140,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Illustrative microorganisms include:

| | |
|---|---|
| Corynebacteria | |
| *Corynebacterium diphtheria* | |
| Pneumococci | |
| *Diplococcus pneumoniae* | |
| Streptococci | |
| *Streptococcus pyogenes* | |
| *Streptococcus salivarus* | |
| Staphylococci | |
| *Staphylococcus aureus* | |
| *Staphylococcus albus* | |
| Neisseria | |
| *Neisseria meningitidis* | |
| *Neisseria gonorrhea* | |
| Enterobacteriaciae | |
| *Escherichia coli* | |
| *Aerobacter aerogenes* | The coliform |
| *Klebsiella pneumoniae* | bacteria |
| *Salmonella typhosa* | |
| *Salmonella choleraesuis* | The Salmonellae |
| *Salmonella typhimurium* | |
| *Shigella dysenteria* | |
| *Shigella schmitzii* | |
| *Shigella arabinotarda* | |
| | The Shigellae |
| *Shigella flexneri* | |
| *Shigella boydii* | |
| *Shigella sonnei* | |
| Other enteric bacilli | |
| *Proteus vulgaris* | |
| *Proteus mirabilis* | Proteus species |
| *Proteus morgani* | |

-continued

| | |
|---|---|
| *Pseudomonas aeruginosa* | |
| *Alcaligenes faecalis* | |
| *Vibrio cholerae* | |
| Hemophilus-Bordetella group | *Rhizopue oryzae* |
| *Hemophilus influenza, H. ducryi* | *Rhizopus arrhizua* Phycomycetes |
| *Hemophilus hemophilus* | *Rhizopus nigricans* |
| *Hemophilus aegypticus* | *Sporotrichum schenkii* |
| *Hemophilus parainfluenza* | *Flonsecaea pedrosoi* |
| *Bordetella pertussis* | *Fonsecacea compact* |
| Pasteurellae | *Fonsecacea dermatidis* |
| *Paeteurella pestis* | *Cladosporium carrionii* |
| *Pasteurella tulareusis* | *Phialophora verrucosa* |
| Brucellae | *Aspergillus nidulans* |
| *Brucella melitensis* | *Madurella mycetomi* |
| *Brucella abortus* | *Madurella grisea* |
| *Brucella suis* | *Allescheria boydii* |
| Aerobic Spore-forming Bacilli | *Phialophora jeanselmei* |
| *Bacillus anthracis* | *Microsporum gypseum* |
| *Bacillus subtilis* | *Trichophyton mentagrophytes* |
| *Bacillus megaterium* | *Keratinomyces ajelloi* |
| *Bacillus cereus* | *Microsporum canis* |
| Anaerobic Spore-forming Bacilli | *Trichophyton rubrum* |
| *Clostridium botulinum* | *Microsporum adouini* |
| *Clostridium tetani* | Viruses |
| *Clostridium perfringens* | Adenoviruses |
| *Clostridium novyi* | Herpes Viruses |
| *Clostridium septicum* | Herpes simplex |
| *Clostridium histolyticum* | Varicella (Chicken pox) |
| *Clostridium tertium* | Herpes Zoster (Shinglee) |
| *Clostridium bifermentans* | Virus B |
| *Clostridium sporogenes* | Cytomegalovirus |
| Mycobacteria | Pox Viruses |
| *Mycobacterium tuberculosis hominis* | Variola (smallpox) |
| *Mycobacterium bovis* | Vaccinia |
| *Mycobacterium avium* | *Poxvirus bovis* |
| *Mycobacterium leprae* | Paravaccinia |
| *Mycobacterium paratuberculosis* | Molluscum contagiosum |
| Actinomycetes (fungus-like bacteria) | Picornaviruses |
| *Actinomyces Isaeli* | Poliovirus |
| *Actinomyces bovis* | Coxsackievirus |
| *Actinomyces naeslundii* | Echoviruses |
| *Nocardia asteroides* | Rhinoviruses |
| *Nocardia brasiliensis* | Myxoviruses |
| The Spirochetes | Influenza(A, B, and C) |
| *Treponeua pallidum Spirillum minus* | Parainfluenza (1–4) |
| *Treponeua pertenue Streptobacillus monoiliformis* | Mumps Virus |
| | Newcastle Disease Virus |
| *Treponeua carateum* | Measles Virus |
| *Borrelia recurrentis* | Rinderpest Virus |
| *Leptospira icterohemorrhagiae* | Canine Dietemper Virus |
| *Leptospira canicola* | Respiratory Syncytial Virus |
| Trypanasomes | Rubella Virus |
| Mycoplasmas | Arboviruses |
| *Mycoplasma pneumoniae* | |
| Other pathogens | Eastern Equine Eucephalitis Virus |
| *Listeria monocytogenes* | Western Equine Eucephalitis Virus |
| *Erysipelothrix rhusiopathiae* | Sindbis Virus |
| *Streptobacillus moniliformis* | Chikugunya Virus |
| *Donvania granulomatis* | Semliki Forest Virus |
| *Bartonella bacilliformis* | Mayora Virus |
| Rickettsiae (bacteria-like parasites) | St. Louis Encephalitis Virus |
| *Rickettsia prowazekii* | California Encephalitis Virus |
| *Rickettsia mooseri* | Colorado Tick Fever Virus |
| *Rickettsia rickettsii* | Yellow Fever Virus |
| *Rickettsia conori* | Dengue Virus |
| *Rickettsia australis* | Reoviruses |
| *Rickettsia sibiricus* | Reovirus Types 1–3 |
| | Retroviruses |
| *Rickettsia akari* | Human Immunodeficiency Viruses (HIV) |
| *Rickettsia tsutsugamushi* | Human T-cell Lymphotrophic Virus I & II (HTLV) |
| *Rickettsia burnetti* | Hepatitis |
| *Rickettsia quintana* | Hepatitis A Virus |
| Chlamydia (unclassifiable parasites bacterial/viral) | Hepatitis B Virus |
| | Hepatitis noA-nonB Virus |
| Chlamydia agents (naming uncertain) | Tumor Viruses |
| Fungi | Rauscher Leukemia Virus |
| *Cryptococcus neoformans* | Gross Virus |
| *Blastomyces dermatidis* | Maloney Leukemia Virus |

*Hisoplaama capsulatum*
*Coccidioides immitis*      Human Papilloma Virus
*Paracoccidioides brasiliensis*
*Candida albicans*
*Aspergillus fumigatus*
*Mucor corymbifer*
(*Absidia corymbifera*)

The term analyte further includes polynucleotide analytes such as those polynucleotides defined below. These include m-RNA, r-RNA, t-RNA, DNA, DNA-RNA duplexes, etc.

The analyte may be a molecule found directly in a sample, such as a body fluid from a host. The sample can be examined directly or may be pretreated to render the analyte more readily detectable. Furthermore, the analyte of interest may be determined by detecting an agent probative of the analyte of interest such as an sbp member complementary to the analyte of interest whose presence will be detected only when the analyte of interest is present in a sample. Thus, the agent probative of the analyte becomes the analyte that is detected in an assay.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Polynucleotide—a compound or composition which is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. The polynucleotide includes nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

Ligand—any organic compound for which a receptor naturally exists or can be prepared.

Ligand analog—a modified ligand which can compete with the analogous ligand for a receptor, the modification providing means to join a ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Specific binding—the specific recognition of one of two different molecules for the other to the exclusion of other molecules. Generally, the molecules have an area on the surface or in a cavity giving rise to specific recognition between the two molecules. The primary binding influence arises from hydrogen bonding. Exemplary of specific binding are antibody-antigen interactions, enzyme-substrate interactons, nucleotide interactions, and so forth.

Non-specific binding—non-covalent binding between molecules that is relatively independent of specific surface structures. Such non-specific binding will usually result from charge or electronic interactions between oppositely charged molecules. Non-specific binding may also result from hydrophobic interactions between molecules.

Ancillary materials—various ancillary materials will frequently be employed in kits and methods in accordance with the present invention. For example, buffers will often be present in the liquid medium, as well as stabilizers for a liquid medium and the other components. Frequently, in addition to these additives, additional proteins may be included, such as albumins, or surfactants, particularly non-ionic surfactants, binding enhancers, e.g., polyalkylene glycols, or the like.

Enzyme—exemplary of enzymes to which the present invention has application are:

| Name & Class | Distribution | Substrate | End-products |
| --- | --- | --- | --- |
| Hydrolases Carbohydrases | | Carbohydrates | |
| 1. Amylase | Pancreas, saliva, malt, etc. | Starch, dextrin, etc. | Maltose and dextrins |
| 2. Lactase | Intestinal juice and mucosa | Lactose | Glucose and galactose |
| 3. Maltase | Intestinal juice, yeast, etc. | Maltose | Glucose |
| 4. Sucrase | Intestinal juice yeast, etc. | Sucrose | Glucose and fructose |
| 5. Emulsin | Plants | β-Glucosides | Glucose, etc. |
| Nucleases | | Nucleic acid and derivatives | |
| 1. Polynucleotidase | Pancreatic juice intenstinal juice etc. | Nucleic acid | Nucleotides |
| 2. Nucleotidase | Intestinal juice and other tissues | Nucleotides | Nucleotides and phosphoric acid |
| 3. Nucleotidase | Animal tissues | Nucleotides | Carbohydrate and bases |
| Amidases | | Amino compounds and amides | |
| 1. Arginase | Liver | Arginine | Ornithine and urea |
| 2. Urease | Bacteria, soybean, jack bean etc. | Urea | Carbon dioxide and ammonia |
| 3. Glutaminase | Liver, etc. | Glutamine | Glutamic acid and ammonia |
| 4. Transaminase | Animal tissues | Glutamic acid and oxalacetic acid, etc | α-Ketoglutaric acid, aspartic acid, etc. |
| Purine Deaminases | | Purine basesa and derivatives | |

-continued

| Name & Class | Distribution | Substrate | End-products |
|---|---|---|---|
| 1. Adenase | Animal tissues | Adenine | Hypoxanthine and ammonia |
| 2. Guanase | Animal tissues | Guanine | Xanthine and ammonia |
| Peptidases | | Peptides | |
| 1. Aminopolypeptidase | Yeast, intestines etc. | Polypeptides | Simpler peptides and a-amino acids |
| 2. Carboxypeptidase | Pancreas | Polypeptides | Simpler peptides and amino acids |
| 3. Dipeptidase | Plant and animal tissues and bacteria | Dipeptides | Amino acids |
| 4. Prolinase | Animal tissues and yeast | Proline peptides | Proline and simpler peptides |
| Proteinases | | Proteins | |
| 1. Pepsin | Gastric juice | Proteins | Proteoses, peptones, etc. |
| 2. Trypsin | Pancreatic juice | Proteins, proteoses, and peptones | Polypeptides and amino acids |
| 3. Cathepsin | Animal tissues | Proteins | Proteoses, and peptones |
| 4. Rennin | Calf stomach | Casein | Paracasein |
| 5. Chymotrypsin | Pancreatic juice | Proteins, proteoses and peptones | Polypeptides and amino acids |
| 6. Papain | Papaya, other plants | Proteins, proteoses, and peptones | |
| 7. Ficin | Fig sap | Proteins | Proteoses, etc. |
| Esterases | | Esters | Alcohols and acids |
| 1. Lipase | Pancreas, castor bean, etc. | Fats | Glycerol and fatty acids |
| 2. Esterases | Liver, etc. | Ethyl butyrate, etc. | Alcohols and acids |
| 3. Phosphatases | Plant and animal tissues | Esters of phosphoric acid | Phosphate and alcohol |
| 4. Sulfatases | Animal and plant tissues | Esters of sulfuric acid | Sulfuric acid and alcohol |
| 5. Cholinesterase | Blood, tissues | Acetylcholine | Choline and acetic acid |
| Iron Enzymes | | | |
| 1. Catalase | All living organisms except a few species of microorganisms | Hydrogen peroxide | Water and oxygen |
| 2. Cytochrome oxidase | All living organisms except a few species of microorganisms | Reduced cytochrome C in the presence of oxygen | Oxidized cytochrome C and water |
| 3. Peroxidase | Nearly all plant cells | A large number of phenols aromatic amines, etc. in the presence of $H_2O_2$ | Oxidation product of substrate and water |
| Copper Enzymes | | | |
| 1. Tyrosinase (poly-phenoloxidase, monophenoloxidase) | Plant and animal tissues | Various phenolic compounds | Oxidation product of substrate |
| 2. Ascorbic acid oxidase | Plant tissues | Ascorbic acid in the presence of oxygen | Dehydroascorbic acid |

-continued

| Name & Class | Distribution | Substrate | End-products |
|---|---|---|---|
| Enzymes Containing Coenzymes I and/or II | | | |
| 1. Alcohol dehydrogenase | Animal and plant tissues | Ethyl alcohol and hols | Acetaldehyde and other aldehydes |
| 2. Malic dehydrogenase | Animal and plant tissues | L() Malic acid | Oxalacetic acid |
| 3. Isocitric hydrogenase | Animal and plant tissues | L-Isocitric acid | Oxalosuccinic acid |
| 4. Lactic dehydrogenase | Animal tissues and yeast | Lactic acid | Pyruvic acid |
| 5. β-Hydroxybutyric dehydrogenase | Liver, kidneys, and heart | L-β-Hydroxybutyric acid | Acetoacetic acid |
| 6. Glucose dehydrogenase | Animal tissues | D-Glucose | D-Gluconic acid |
| 7. Robison ester dehydrogenase | Erythrocytes and yeast | Robison ester (hexose-6-phosphate | Phoaphohexonic |
| 8. Glycerophosphate dehydrogenase | Animal tissues | Glycerophosphate | Phosphogylceril acid |
| 9. Aldehyde dehydrogenase | Liver | Aldehydes | Acids |
| Enzymes which Reduce Cytochrome | | | |
| 1. Succinic dehydrogenase (as ordinarily prepared) | Plants, animals and microorganisms | Succinic acid | Fumaric acid |
| Yellow Enzymes | | | |
| 1. Warburg's old yellow enzyme | Yeast | Reduced coenzyme II | Oxidized coenzyme II and reduced yellow enzyme |
| 2. Diaphorase | Bacteria, yeasts, higher plants, and animals | Reduced coenzyme I | Oxidized coenzyme I and reduced yellow diaphorase |
| 3. Haas enzyme | Yeast | Reduced coenzyme II | Oxidized coenzyme II and reduced yellow enzyme |
| 4. Xanthine oxidase | Animal tissues | Hypoxanthine xanthine, aldehydes, reduced coenzyme I, etc. | Xanthine, uric acid, acids, oxidized coenzyme I, etc. In presence of air, $H_2O_2$ |
| 5. D-amino acid oxidase | Animal tissues | D-Amino Acids + $O_2$ | α-Keto-acids + $NH_3$ + $H_2O_2$ |
| 6. L-Amino acid oxidases | Animals, snake venoms | L-amino acids | Keto acids ammonia |
| 7. TPN-Cytochrome C reductase | Yeast, liver | Reduced coenzyme II and cytochrome C | Oxidized coenzyme I and reduced cytochrome C |
| 8. DPN Cytochrome C recuctase | Liver, yeast | Reduced coenzyme I and cytochrome C | Oxidized coenzyme I and reduced cytochrome C |
| Hydrases | | | |
| 1. Fumarase | Living organisms in general | Fumaric acid + $H_2O$ | L-Malic acid |
| 2. Aconitase | Animal and plants | Citric acid | cis-Aconitic acid and L-isocitric |

| Name & Class | Distribution | Substrate | End-products |
|---|---|---|---|
| 3. Enolase | Animal tissues and yeast | 2-Phospho-glyceric acid | acid Phospyruvic acid + H$_2$O |
| Mutases | | | |
| 1. Glyoxalase | Living organisms in general | Methyl glyoxal and other substituted glyoxals | D(-) Lactic acid |
| Desmolases | | | |
| 1. Zymohexase (aldolase) | All cells | Fructose-1.6-diphoxphate | Dihydroxy-acetone phosphoric acid and phospho-glyceric acid |
| 2. Carboxylase | Plant tissues | Pyruvic acid | Acetaldehyde and CO$_2$ |
| 3. β-Keto carboxylases | Animals, bacteria, plants | β-Keto-acids | α-Keto acids |
| 4. Amino acid decarboxylases | Plants, animals, bacteria | L-Amino acids | Amines and CO$_2$ |
| 5. Carbonic anhydrase | Erythrocytes | Carbonic acid | CO$_2$ + H$_2$O |
| Other Enzymes | | | |
| 1. Phosphorylase | Animal and plant tissues | Starch or glycogen and phosphate | Glucose-1-phosphate |
| 2. Phosphohexo-isomerase | Animal and plant tissues | Glucose-6-phosphate | Fructose-6-phosphate |
| 3. Hexokinase | Yeast, animal tissues | Adenosine-triphosphate | Adenosined-iphosphate + glucose-6-phosphate |
| 4. Phosphoglu-comutase | Plant and animals | Glucose-1-phosphate | Glucose-6-phosphate |

Of the various enzymes, the following table indicates enzymes of particular interest set forth in accordance with the I.U.B. classification.

1. Oxidoreductases
   1.1 Acting on the CH—OH group of donors
      1.1.1 With NAD or NADP as acceptor
         1. alcohol dehydrogenase
         6. glycerol dehydrogenase
         26. glyoxylate reductase
         27. L-lactate dehydrogenase
         37. malate dehydrogenase
         49. glycose 6-phosphate dehydrogenase
         17. mannitol 1-phosphate dehydrogenase
      1.1.2 With cytochrome as an acceptor
         3. L-lactate dehydrogenase
      1.1.3 With O$_2$ as acceptor
         4. glucose oxidase
         9. galactose oxidase
   1.9 Acting on the CH—NH$_2$ group of donors
      1.4.3 With O$_2$ as acceptor
         2. L-amino acid oxidase
         3. D-amino acid oxidase
   1.6 Acting on reduced NAD or NADP as donor
      1.6.99 With other acceptors diaphorase
      1.10 Acting on diphenols and related substances as donors
         1.10.3 With O$_2$ as acceptor
            1. polyphenol oxidase
            3. ascorbate oxidase
   1.11 Acting on H$_2$O$_2$ as acceptor
      1.11.1
         6. catalase
         7. peroxidase
3. Hydrolases
   3.1 Acting on ester bonds
      3.1.1 Carboxylic ester hydrolases
         7. cholinesterase
      3.1.3 Phosphoric monoester hydrolases
         1. Alkaline phosphatase
      3.1.4 Phosphoric diester hydrolases
         3. phospholipase C
   3.2 Acting on glycosyl compounds
      3.2.1 Glycoside hydrolases
         1. α-amylase
         4. cellulase
         17. lysozyme
         23. β-galactosidase
         27. amyloglucosidase
         31. β-glucuronidase
   3.4 Acting on peptide bonds
      3.4.2. Peptidyl-amino acid hydrolase
         1. carboxypeptidase A
      3.4.4 Peptidyl-peptide hydrolase
         5. α-chymotrypsin
         10. papain
   3.5 Acting on C—N bonds other than peptide bonds
      3.5.1 In linear amides
         5. urease
   3.6 Acting on acid anhydride bonds
      3.6.1 In phosphoryl-containing anhydrides
         1. inorganic pyrophosphatase
4. Lyases
   4.1 Carbon-carbon lyases
      4.1.2 Aldehyde lyases
         7. aldolase
   4.2 Carbon-oxygen lyases
      4.2.1 Hydrolases
         1. carbonic anhydrase
   4.3 Carbon-nitrogen lyases
      4.3.1 Ammonia lyases
         3. histidase Glucose-6-phosphate dehydrogenase (G6PDH)—an enzyme having the I.U.B. classification of oxidoreductase acting on the CH—OH group of donors having glucose-6-phosphate as a substrate. In general, any source or form of G6PDH can be used. However, it is especially preferred to select a microbial source which produces an enzyme which can use a cofactor that is not effective with G6PDH endogenous to a test sample, such as a mammalian body fluid. Microbial sources for G6PDH include *Leuconostoc mesenteriodes, Pseudomonas aeuroginosa*, Hydrogenomonas H16, *Thiobacillus ferrooxidans, Bacillus stearothermophilus, Bacillus mageratum, Zymomonas mobilis*, and the like. Particularly preferred are those G6PDH molecules that are able to utilize both NADP and NAD. Since G6PDH from animal sources normally is able to utilize only NADP, one can limit interference from endogenous G6PDH by employing NAD as the cofactor, when enzyme conjugates are employed in immunoassays. G6PDH from *Leuconostoc mesenteriodes* and *Zymomonas mobilis* are particularly preferred for this reason.

Antibody—an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal), by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antibody for an enzyme—an antibody specific for an enzyme. Such antibody may be formed by immunization against whole or modified enzyme by any available technique. Thus, an appropriate antibody source can be stimulated to produce anti-enzyme by immunization with whole enzyme, aggregated or otherwise polymerized enzyme, enzyme fragments (e.g., by selecting antigenic determinants from the enzyme), synthetically prepared antigenic determinants, and so forth.

Usually, antibodies will be obtained by conventional antiserum techniques, monoclonal techniques, or recombinant nucleotide cloning techniques. Antiserum containing an anti-enzyme is obtained by well-established techniques, involving immunization of an animal, such as a rabbit, guinea pig, or goat, with an appropriate immunogen obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Weinryb and Shroff, Drug Metab. Rev. 10: 271–283 (1975); Broughton and Strong, Clin. Chem. 22: 726–732 (1976); and Playfair, et al., Br. Med. Bull. 30: 24–31 (1974).

Such antibodies can also be obtained by somatic cell hybridization techniques, such antibodies being commonly referred to as monoclonal antibodies. Monoclonal antibodies useful in the method of the invention may be produced according to the standard techniques of Köhler and Milstein, Nature 265: 495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). For example, whole or modified enzyme can be used as the immunogen. Samples of the antigen preparations are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, microtiter wells, and the supernatant is screened for monoclonal antibodies having the desired specificity. Alternatively, the sequences coding for antibody binding sites can be excised from the chromosome DNA and inserted into a cloning vector which can be expressed in bacteria to produce recombinant proteins having the corresponding antibody binding sites.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Various conventional ways exist for isolation and purification of the monoclonal antibodies from other proteins and other contaminants (see Köhler and Milstein, supra).

Also included within the scope of the invention and the definition of monoclonal antibody are useful binding fragments of the monoclonal antibody such as Fab, F(ab')$_2$, Fv, and so forth. The antibody fragments are obtained by conventional techniques. For example, useful binding fragments may be prepared by peptidase digestion of the antibody using papain or pepsin.

The antibodies can be from a murine source, other mammalian source including human, rat, or other sources, or combinations thereof. IgG and IgM classes of antibodies, as well as other classes such as IgA, IgE, and the like, including isotypes within such classes and also other isotypes within the IgG and IgM classes may be employed.

Antibody to G6PDH—As used in the context of the present invention, the term "anti-G6PDH" shall be understood to mean an antibody capable of binding with G6PDH or a derivative or modification of such an antibody which retains the capability of binding with G6PDH. Thus, in general any substance which comprises one or more G6PDH-specific binding sites from an antibody can be used.

Normally the G6PDH to be used in an assay will be used as the immunogen although G6PDH from related organisms may be used in some cases. Alternatively, G6PDH conjugates with haptens can be used.

As mentioned above, one aspect of the present invention concerns a method for stabilizing a conjugate of an enzyme and a member of a specific binding pair (enzyme conjugate). The method comprises the step of combining the enzyme conjugate with an effective amount of an antibody for the enzyme where the antibody does not substantially inhibit the activity of the enzyme. Generally, an effective amount of the antibody for the enzyme is that which results in substantial stabilization of the enzyme of the enzyme conjugate such that loss of enzyme activity in the conjugate is minimized during long periods of storage and handling and adverse storage and handling conditions, such as elevated temperatures, and the like. Usually about at least equal molar concentrations of antibody and enzyme are used. Preferably, the antibody is present in 5 to 10-fold or greater excess and will generally be present in concentrations at least equal to, and preferably 5 to 10-fold greater than, the antibody enzyme complex dissociation constant. In general, antibody concentration sufficient to bind at least 90% of the enzyme conjugate, preferably 95%, usually at least 97%, will be employed.

The antibodies of the invention can be prepared by any of the techniques described above. The antibody preparations are then screened to determine their respective binding affinities and specificities for the enzyme as well as whether or not such antibodies inhibit the activity of the enzyme. The screening procedures utilized are well-known in the art and include, by way of example and not limitation, ELISA assays utilizing the enzyme in question bound to a support and enzyme thermal protection assays that involve combining the anti-enzyme antibody with an enzyme conjugate, incubating the combination, and determining enzyme activity. Additionally, the antibodies to enzyme can be studied to determine whether such antibodies interfere with the binding of an sbp member with a complementary sbp member in an enzyme conjugate containing such complementary sbp member.

The antibody for the enzyme should not substantially inhibit the activity of the enzyme. This means that the antibody for the enzyme should not reduce the activity of an enzyme by more than 25 percent, preferably not more than 5 percent, and most preferably will not cause any reduction in enzymes activity. Furthermore, the preferred antibody for the enzyme will not substantially inhibit the ability of the enzyme conjugate of an sbp member to bind to complementary sbp member such as an antibody, or to hybridize to a polynucleotide complementary to the sbp member where the sbp member is a polynucleotide. Accordingly, the antibody for the enzyme should not inhibit the ability of an sbp member to modulate the activity of an enzyme conjugate more than 50 percent, preferably not more than 25 percent, and desirably should not affect the modulation.

The combination of the antibody for the enzyme and the enzyme conjugate may be in the lyophilized or dry state or may be in a liquid medium, usually aqueous, but may contain up to 40 volume percent of an organic cosolvent. The pH for the medium will usually be in the range of 4 to 11, more usually in the range of about 5 to 10, and preferably in the range of about 6.5 to 9.5. Various buffers may be used to achieve the desired pH. In general, the medium and buffers and the like are similar to those described herein for the performance of an assay in accordance with the present invention.

The present invention also provides an improvement in conducting an assay for an analyte. The assay comprises the steps of combining a medium suspected of containing the analyte or an agent probative of the analyte with a reagent that is an enzyme conjugate and determining the enzyme activity of the enzyme by use of an antibody for the member and a substrate for the enzyme as a indication of the presence or amount of the analyte. The improvement comprises employing as the reagent an immune complex of the enzyme conjugate and an antibody for the enzyme where the antibody does not substantially inhibit the activity of the enzyme.

The method and compositions of the invention may be adapted to most assays involving sbp members such as ligand-receptor, e.g., antigen-antibody reactions, polynucleotide binding assays, and so forth. The assays may be homogeneous or heterogeneous. In a homogeneous assay approach, the sample may be pretreated if necessary to remove unwanted materials. The immunological reaction usually involves an sbp member complementary to the analyte, which is an sbp member, an enzyme labeled sbp member (enzyme conjugate), and the sample of interest. Usually the enzyme is conjugated to a hapten, normally a derivative of the analyte and the sbp member complementary to the analyte is an antibody. The signal arising from the label is modified, directly or indirectly, upon the binding of the antibody to the labeled analyte. Both the immunological reaction and detection of the extent thereof are carried out in a homogeneous solution.

In accordance with the present invention, a composition is employed in place of enzyme labeled sbp member. The composition comprises enzyme labeled sbp member and antibody for the enzyme that does not substantially inhibit the activity of the enzyme and does not interfere substantially with the inhibition of enzyme activity upon the binding of the complementary sbp member with the enzyme labeled sbp member. Exemplary of homogeneous assays are the enzyme modulated immunoassay technique (EMIT®) described in U.S. Pat. No. 3,817,837, the disclosure of which is incorporated herein by reference, and the like.

A preferred enzyme for the enzyme modulated immunoassay technique G6PDH as described in U.S. Pat. No. 3,875,011. The G6PDH is usually conjugated to an analyte analog to form an enzyme conjugate that is then employed as one reagent in the assay for the analyte. Other preferred enzymes include malate dehydrogenese and glucose dehydrogenase, galactosidase, triose phosphate isomerase.

In a heterogeneous assay approach, the reagents comprise a sample suspected of containing an analyte, which is an sbp member, a complementary sbp member, and means for producing a detectable signal involving an enzyme conjugate. These compounds are generally placed in contact with a support, such as a plate or a slide, to which the conjugate binds in relation to the presence of analyte in the sample. The support is then separated from the liquid phase and either the support phase or the liquid phase is examined for a detectable signal employing means for producing such signal. For example, the complementary sbp member or an sbp member analogous to the analyte can be conjugated to an enzyme and a second sbp member complementary to the analyte can be bound to the support. In any such instance, a composition in accordance with the present invention can be substituted for the enzyme conjugate reagent. Exemplary of heterogeneous immunoassays are the enzyme-linked immunoassays, such as the enzyme-linked imunosorbent assay (ELISA, see U.S. Pat. Nos. 3,654,090; 3,839,153; 3,850,752; 4,016,043; and Re 29,169; the disclosures of which are incorporated herein by reference), and the like.

For a more detailed discussion of the above immunoassay techniques, see "Enzyme-Immunoassay," by Edward T. Maggio, CRC Press, Inc., Boca Raton, Fla. 1980.

The assay for the analyte will normally be carried out in an aqueous buffered medium at a moderate pH, generally that which provides optimum assay sensitivity. As explained above, the assay can be performed either without separation (homogeneous) or with separation (heterogeneous) of any of the assay components or products.

The aqueous medium may be solely water or may include from 0 to 40 volume percent of a cosolvent. The pH for the medium will usually be in the range of about 4 to 11, more usually in the range of about 5 to 10, and preferably in the range of about 6.5 to 9.5. The pH will usually be a compromise between optimum binding of the binding members and the pH optimum for other reagents of the assay such as members of the signal producing system.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred.

Moderate temperatures are normally employed for carrying out the assay and usually constant temperatures during the period of the measurement, particularly for rate determinations. Incubation temperatures will normally range from about 5° to 45° C., more usually from about 15° to 40° C. Temperatures during measurements will generally range from about 10° to 50°, more usually from about 15° to 40° C.

The concentration of analyte which may be assayed will generally vary from about $10^{31\ 4}$ to $10^{-15}$M, more usually from about $10^{-6}$ to $10^{-14}$M. Considerations, such as whether the assay is qualitative, semiquantitative or quantitative, the particular detection technique and the concentration of the analyte of interest will normally determine the concentrations of the various reagents.

While the concentrations of the various reagents in the assay medium will generally be determined by the concentration range of interest of the analyte, the final concentration of each of the reagents will normally be determined empirically to optimize the sensitivity of the assay over the range. That is, a variation in concentration of the analyte which is of significance should provide an accurately measurable signal difference.

While the order of addition may be varied widely, there will be certain preferences depending on the nature of the assay. The simplest order of addition is to add all the materials simultaneously and determine the effect that the assay medium has on the signal producing system as in a homogeneous assay. Alternatively, the reagents can be combined sequentially. Optionally, an incubation step may be involved subsequent to each addition, generally ranging from about 30 seconds to 6 hours, more usually from about 2 minutes to 1 hour.

In a homogeneous assay after all of the reagents have been combined either simultaneously or sequentially, the affect of the assay medium on the signal producing system is determined. The effect of the assay medium on the signal producing system is related to the amount of the monoepitopic analyte in the sample tested. For this purpose the novel reagent of the invention should be soluble in an aqueous medium and is added preferably combined with the sample and an sbp member complementary to the analyte. The amount of the reagent of the invention employed in a homogeneous assay depends on the nature of the analyte and of the other reagents. An example of such amounts of reagents is set out in U.S. Pat. No. 3,817,837, particularly at column 4, the relevant disclosure of which is incorporated herein by reference. The use of the reagent of the invention in homogeneous assays increases the sensitivity of the assays by maintaining the activity of the enzyme in the enzyme reagent during storage.

The present invention further encompasses compositions comprising an immune complex comprised of (1) a conjugate of an enzyme and a member of a specific binding pair and (2) an antibody for the enzyme which does not substantially inhibit the enzyme.

Another aspect of the present invention relates to kits useful for conveniently performing the assay method of the invention for determining the presence or amount of an analyte in a sample suspected of containing the analyte. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. The kit comprises as one reagent a composition in accordance with the invention. As mentioned above, for homogeneous immunoassays the preferred enzymes of the enzyme conjugate are dehydrogenases, preferably G6PDH, malate dehydrogenase and glucose dehydrogenase. The enzyme is preferably conjugated to an analog of a drug such as a drug of abuse or a therapeutic drug and is bound to an anti-enzyme antibody, usually a monoclonal, anti-enzyme antibody. For homogeneous enzyme immunoassays, the kit can further comprise an antibody for the drug.

The kit can further include other separately packaged reagents for conducting an assay including members of the signal producing system such as enzyme substrate, supports as in ELISA assays and DNA probe assays, ancillary reagents and so forth. A support can be a porous or nonporous water insoluble material. The support can be hydrophilic or capable of being rendered hydrophilic and includes inorganic powders, natural polymeric materials synthetic or modified naturally occurring polymers, such as plastics; glass; ceramics; metals and the like. Various ancillary materials will frequently be employed in kits in accordance with the present invention.

EXAMPLES

The invention is demonstrated further by the following illustrative examples. Parts and percentages used herein are by weight unless otherwise specified. Temperatures are in degrees centigrade (°C).

Example 1

Preparation of Monoclonal Antibodies to G6PDH

A. Abbreviations and Definitions

| | |
|---|---|
| Δ Ao | Initial absorbance reading on Stasar instrument |
| Δ Af | Final absorbance reading on Stasar instrument (sum of four readings every 10 sec. after 10 sec. delay) |
| Ab(s), MAb(s) | Antibody(ies), Monoclonal Antibody(ies) |
| Ag 8.653 | Nonsecretor myeloma cell line from the A.T.C.C. |
| CFA | Complete Freund's Adjuvant |
| $DH_2O$ | Millipore Deionized Water |
| Diluent A | Reagent A EMIT ® Assay Buffer, 10 g/L rabbit serum albumin, 6.66 g/L Trizma base, 0.5 g/L sodium azide, 0.05 g/L thimerosal, 26.54 g/L nicotine adenine dinucleotide, 18.62 g/L glucose-6-phosphate |
| DMEM | Dulbecco's Modified Eagle's Medium |
| DMSO | Dimethylsulfoxide |
| Diethanolamine Buffer | 96 mL/L diethanolamine, 49 g/L magnesium chloride-$6H_2O$; adjust pH to 9.8 |
| ELISA | Enzyme-linked Immunosorbent Assay |
| FCS | Fetal Calf Serum |
| G6PDH | Glucose-6-phosphate dehydrogenase |
| HAT | Super DMEM with 0.1 mM hypoxanthine, 16 μM thymidine, 0.8 μM aminopterin |
| HBSS | Hank's Balanced Salt Solution |
| HT | Super DMEM with 0.1 mM hypoxanthine, 16 μM thymidine |
| IFA | Incomplete Freund's Adjuvant |
| NSS | Normal Sheep Serum |
| PBS | Phosphate-buffered saline, 0.01M phosphate, 0.15M sodium chloride, 0.02% sodium azide, pH 7.2 |
| PEG | Polyethylene glycol |
| QUN | Quinidine |
| RBF/Dn system | RBF/Dn mice [Pb (1.3) 1 BnrRb (8.12) 5 Bnr, Rb (9.14) 6 Bnr] from Jackson Labs; reference - Taggart et. al., (1983) Science, 219, 1228–1230. HL-1 myeloma. (Ventrex No. VBPG 007–653, Lot 01415A) HL-1 Media (Ventrex No. VBPG 001) |
| RSA | Rabbit serum albumin |
| RT | Room temperature |
| Super DMEM | DMEM with 10% FCS, 10% NCTC 109, |

|  |  |
|---|---|
|  | 50 mg/mL gentamicin, 4.0 mM L-glutamine, 1.0 mM oxaloacetic acid, 0.45 mM pyruvate, 10 µg/mL bovine insuline, 25 mM HEPES |
| THP | Theophylline |
| Tris | 0.055M Tris, pH 8.0 (Sigma #T-1503) |
| Wash Buffer | 0.05% Tween 20 in PBS |
| 0.055M Tris, pH 8.0 | 24.228 g/100 mL Tris (MW 121.4), 9.71 mL/100 mL 12N HCl; adjust pH to 8.0 |

B. Materials and Methods

1. Immunizations

Initially, 25 Balb/c mice were immunized intraperitoneally with either 100 µg (12 "high dose" mice) or 10 µg (12 "low dose" mice) of G6PDH. The immunogen was a 50:50 mixture of United States Biochemicals (USB) Cat. No. 16190 and Cooper Cat. No. 9869 G6PDH in CFA, boosted once with 100 or 10 µg (high or low dose mice) in IFA at 2 weeks, then at monthly intervals after that. Titers were checked by Ouchterlony double immunodiffusion against 1 and 3 mg/mL of both Cooper and USB G6PDH with sera obtained from the mice at various intervals.

A second set of eight CB6/F1 mice were immunized with 100 µg of G6PDH (50:50 Cooper:USB) in CFA, boosted twice with 100 µg in IFA at 2-week intervals, then monthly after that.

A final set of eight RBF/Dn mice [Rb(1.3) 1 BnrRb(8.12) 5 Bnr, Rb(9.14) 6Bnr, from Jackson Labs] was immunized with 100 µg 50:50 G6PDH in CFA, then boosted twice with 100 µg in IFA at 2- to 3-week intervals, then monthly after that (Taggart, et al., (1983) *Science*, 219: 1228–1230).

2. Fusions

Thirteen fusions were completed. Parental myeloma P3X63 Ag 8.653 (8.653) was used for Fusions 1 to 11, with the standard PEG fusion procedure as described below. Fusions 12 and 13 were done with the RBF/Dn mice and the HL-1 myeloma (Ventrex Cat. No. VBPG 007-653, Lot No. 01415A) as described below.

The 8.653 fusions were done as follows:

Spleens were aseptically removed from the immunized mice and trimmed of extraneous tissue, then sliced into a sterile homogenizer, and homogenized with five to seven passes in Super DMEM. The spleen cell suspension was poured off into a tube with $2.5 \times 10^7$ 8.653 cells per spleen in DMEM (no FCS) and centrifuged at 1000 rpm for 5 min. The cells were washed once with 20 mL DMEM (no FCS) then gently resuspended in 2 mL PEG per spleen. The tube was swirled gently by hand for one min., then 1 mL DMEM (no FCS) was added and mixed, followed by 5–7 mL of Super DMEM. The tube was allowed to sit undisturbed for 6 min., then centrifuged for 5 min. at 800–1000 rpm. The cells were resuspended in 120 mL Super HAT medium per spleen and plated at 200 µL/well into six Costar 96-well tissue culture plates per spleen. The plates were incubated at 37° C. in 7% $CO_2$ and observed after 3–7 days, then daily for hybridoma growth. The cultures were fed on Day 4 or 5 with Super HAT containing peritoneal exudate feeder cells, then on Days 7 or 8 and 10 with Super HT (no aminopterin) by removing 150 µL of spent media and replacing it with 175 µL new media.

The RBF/Dn x HL-1 fusions were done as follows:

Spleens were removed and treated as for the 8.653 fusion (above), using HL-1 media (Ventrex Cat. No. VBPG 001, serum free, with 2 mM L-glutamine and 50 µg/mL gentamicin added) in place of Super DMEM. The spleen cells were added to about $7 \times 10^6$ to $1 \times 10^7$ HL-1 myeloma cells per spleen in HL-1 media and the fusion completed as before, using 1 mL of HL-1 media per spleen, followed by 5 mL of HL-1 media with 1% FCS after the PEG had been added. After centrifuging, the cells were resuspended in 120 mL HL-1 media containing AAT ($7.5 \times 10^{-5}$M adenine, 0.8 µM aminopterin, 16 µM thymidine) per spleen. The fusions were fed as before, using HL-1 with AAT (no feeder cells for Fusion 12, half of Fusion 13 with feeder cells, and half with 1% FCS) the first time, then HL-1 with AT (no aminopterin) after that.

3. Screening

Fusions were initially screened by a Forward ELISA using a 50:50 mixture of USB and Cooper G6PDH as a plate coat. This initial screen was followed by an Enzyme Thermal Protection Assay described below. Those wells showing protection were cloned and screened by ELISA. A final protection assay was done when clones were stabilized. Further study of the MAbs was done by an EMIT® assay.

a. Forward ELISA (1) Costar EIA plates were coated with 50 µL/well of a 50 µg/mL equal mixture of Cooper and USB G6PDH in PBS, pH 7.2, for 1–2 hrs. at 37° C. The plates were blocked for 1–4 hrs. at room temperature (RT), to overnight at 4° C., with 200 µL/well of 1% NSS in PBS, pH 7.2. Prior to use, they were washed once with ELISA wash buffer.

(2) Fifty µL/well of culture supernatants of ascites Ab were added to the wells and the plates incubated for 1 hr. at 37° C.

(3) The plates were washed three times with ELISA wash buffer; then, 50 µL/well of 1000-fold diluted goat anti-mouse IgG+IgM (γ+µ+ light-chain specific)-alkaline phosphatase conjugate (Tago Cat. No. 6543) in PBS, pH 7.2, were added to the wells and the plates incubated 1 hr. at 37° C.

(4) The plates were washed five times with ELISA wash buffer; then, 75–100 µL/well of substrate, p-nitrophenylphosphate disodium (Sigma Cat. No. 1040, 60 mg/100 mL) in diethanolamine buffer, pH 9.8, were added to the wells.

(5) The plates were shaken for 30–90 min., then read at 405 nm. Those wells with OD greater than twice the background were chosen for further study or cloning.

b. G6PDH Enzyme Thermal Protection Assay (1) Two hundred µL of sample (supernatant or diluted ascites), Tris-RSA buffer (55 mM Tris, 1% RSA, pH 8.0), Super DMEM, and 1:10 diluted G6P III E2 ascites Ab control was placed in tubes with 400 µL of QUN-G6PDH conjugate utilized in the EMIT® quinidine assay sold by Syva Company; (1 µL in 5 mL Tris-RSA buffer) and mixed.

(2) Duplicate 200 µL samples from each tube in step b(1) were placed into two sets of tubes and incubated for 10 min.—one set at 40° C. in water bath—the other set at RT.

(3) The tubes were immediately placed in an ice-water bath.

(4) The absorbance at 340 nm was read on the Stasar system set up as follows:

(a) Crohn cups were set up with 300 µL of Tris buffer, pH 8.0.

(b) Sample (50 µL) was added to the cup along with 250 µL of Tris using the pipetter-diluter.

(c) Substrate concentrate (50 µL; 2X Diluent A, Syva Company No. 6A353) plus 250 µL Tris were added with the pipetter-diluter and the sample read.

(d) The readings were done with a delay of 10 sec. ($A_o$) and then after 40 sec. ($\Delta A_f$ with the Stasar set in the two-point mode, absorbance setting.

(5) The results were calculated as follows:
  (a) The $\Delta A_f$ for each sample at RT and 40° C. was recorded. The percent (%) enzyme rate of the Tris buffer at RT was assigned the value of 100% (control, C-RT).
  (b) The % rates for all samples and controls at RT and 40° C. were determined by dividing their $\Delta A_f$ values by that of the Control and multiplying by 100: ($\Delta A_f$ sample/$\Delta A_f$ C-RT)100.
  (c) The % enzyme rate of the samples at 40° C. was then compared to the % rate for Tris and Super DMEM at 40° C. as well as to the % rate of that sample at RT. Those which showed a greater percentage of activity remaining (i.e., % at 40° C. greater than 50%) were selected.

(4) Cloning

All hybridomas were cloned by serial dilution three to four times prior to stabilization. Cells from positive wells were diluted 1:10 or 1:100 into wells of Costar 24-well culture plates depending on the cell density (those hybridomas with few cells were grown to higher density in 24 well cultures prior to cloning). Fifty µL of this dilution were placed into the first well of a microtiter plate containing 200 µL Super DMEM per well. Fifty µL from this row, after mixing with the multichannel pipetter, were transferred to the second row, and the procedure continued down the plate for either four rows (half a plate) or eight rows (full plate). Visual examination showed that the first row had 5 to 20 cells/well, and the third or fourth row had only one to two cells/well, at most. Plates were incubated at 37° C. in 7% $CO_2$ and rescreened by ELISA after 5 to 10 days.

5. Freezing

Stable hybridomas were frozen as described below, with four vials frozen per hybridoma, and larger quantities frozen for important hybridomas. Briefly, cells were expanded from 96-well culture into 24-well cultures, T-25 flasks, and finally into T-75 flasks. Cells from log-phase cultures were counted in Trypan Blue in a hemacytometer, and the desired number of viable cells (usually $10^6$–$10^7$ per vial) centrifuged at 1000 rpm for 10 min. in the Beckman TJ-6 centrifuge. The supernatant was poured off and the cell pellets placed in an ice bath. The cells were resuspended in cold, sterile 10% DMSO–90% Super DMEM and aliquoted into labeled 2-mL Nunc vials, 1 mL vial, and placed in an ice bath. Cells were frozen by placing them in a styrofoam container in the Queue –120° C. freezer overnight, which approximates a cooling rate of –1° per min. Vials were then stored in liquid nitrogen containers.

6. Ascites

Ascites was produced for the six hybridomas listed in Table 2 and these Abs retested for enzyme protection and EMIT assay performance. Ascites was produced in Balb/c mice primed with 0.5 mL pristane (Sigma Cat. No. T-7640; 2,6,10,14-tetramethylpentadecane) per mouse 1 to 4 weeks prior to injection with hybridoma cells. Cells were expanded as for freezing, then $10^6$ to $10^7$ cells per mouse were centrifuged at 100 rpm for 10 min. in the Beckman TJ-6 centrifuge. The supernatant was poured off and the cells resuspended in the required volume of Super DMEM (05. mL/mouse, usually 2–4 mice per cell line). The pristane-primed mice were injected with the cells intraperitoneally, then observed for tumor development. Tumors were usually evident after 10–14 days. The ascites was tapped by inserting a 16- or 18-gauge needle into the side of the abdomen and collecting the fluid into a test tube. Mice were tapped approximately every other day.

The ascites was allowed to clot for 30 min. to 1 hr. at RT, then centrifuged at 2500 rpm at 4° C. in the Beckman TJ-6 centrifuge for 15 to 30 min. This clear fluid was removed into labeled tubes and stored at –20° C.

7. Characterization

The subclasses of the hybridoma Abs were determined with either the Zymed Mono Ab ID EIA kit (No. 90-6550, Fusions 1–7) or with the Southern Biotechnology SBA Clonotyping System I kit (No. 5010-AP, Fusions 8–10) as described in their instructions.

The procedure for the Zymed kit used plates coated with G6PDH as for the standard ELISA. Fifty µL/well of spent culture supernatants were allowed to bind to the plates, followed by 50 µL/well of either normal rabbit serum control or rabbit anti-mouse subclass specific Abs ($IgG_1$, $IgG_{2a}$, $IgG_{2b}$, $IgG_3$, IgM, IgA, and κ and γ light chains). This was followed by goat anti-rabbit peroxidase conjugate and ABTS-peroxide substrate (supplied in kit). The $OD_{414}$ was read and the subclass determined.

The procedure for the Southern Biotechnology kit was similar, using G6PDH-coated ELISA plates and 50 µL/well of supernatant Ab. This was followed by 50 µL/well of either goat anti-mouse IgG Ab-alkaline phosphatase conjugate (not subclass specific) or goat anti-mouse subclass-specific Ab-alkaline phosphatase conjugates ($IgG_1$, $IgG_{2a}$, $IgG_{2b}$, $IgG_3$, IgM, and κ and γ light chains), then p-nitrophenyl phosphate substrate. The $OD_{405}$ was read and the subclasses determined.

G6PDH Source Specificity

The ability of the MAbs to bind to either of the two G6PDH enzymes, USB or Cooper, was tested by a Forward ELISA. The standard ELISA was run with the following changes:
  (a) The EIA plates were coated with 50 µL/well of a 100 µg/mL solution of either Cooper or USB G6PDH in PBS, pH 7.2, as for the Forward ELISA.
  (b) Fifty µL/well of diluted ascites Ab were added to the wells of the plates in 1:2 steps from a 1:100 dilution to 1:204,800 dilution, 12 wells per Ab, and the plates incubated 1 hr. at 37° C. Each Ab was exposed to both enzymes.
  (c) Goat anti-mouse alkaline phosphatase conjugate was added as for the Forward ELISA.
  (d) Substrate was added as for the Forward ELISA.
  (e) The plates were read for the Forward ELISA.

The ELISA binding curves were determined for various dilutions of anti-G6PDH MAbs (1:2 dilutions of ascites Ab from 1:100 to 1:204,800 across the ELISA plate) to either the USB or Cooper G6PDH enzyme used as a plate coat. Only the 10-4D6 Ab showed a significant difference in binding between the two enzymes, indicating a preference for the USB G6PDH.

C. Results

1. Immunizations

When the titers from the first set of 25 Balb/c mice were checked by Ouchterlony Double Immunodiffusion 7 days after the week-4 immunization, only the high-dose (100 µg) mice showed a visible precipitin band. Fusions 1 and 2 were done with these mice. Sera titers were again checked 10 days after the week 8 boost, with some response now seen in the low-dose (10 µg) mice. Nine of the low-dose mice were switched to 100 µg boosts at this point. Fusions 3 and 4 were again done with high-dose mice. Eight days after the week-12 boost, sera titers were rechecked with all but three mice (low, then switched to high doses) showing good precipitin reactions. Fusions 5 and 6 were done with the original high-dose mice and Fusion 7 with mice receiving only the low dose. Fusion 9 was done with mice that received low then high doses.

Titers from the second set of eight CB6/F1 mice were checked by Ouchterlony Double Immunodiffusion with sera obtained from the mice 6 days after the week-6 immunizations. All mice had very good reactions. Fusions 8, 10, and 11 were done with these mice.

Titers from the final set of eight RBF/Dn mice were checked by Ouchterlony with the sera obtained from the mice 6 days after the week-6 immunization. All mice had very good titers. Fusions 12 and 13 were done with these mice.

2. Fusions

A summary of the fusions is shown in Table 1. Only fusions using Balb/c or CB6/F1 mice produced any Ab-producing cells on the initial screens (Fusions 1, 3, 4, 5, 6, 7, 8, 10, and 11). From these, only eight hybridomas were stabilized (Table 2). The most successful fusions used mice immunized with the higher dose, 100 µg, of G6PDH (Fusions 1, 3, 4, 5, 6, 8, 10, and 11). Fusions done with the lower-dose (10 µg) mice or mice which initially received 10 then 100 µg G6PDH were generally unsuccessful in producing initial Ab-positive wells or stabilized hybridomas (Fusions 7 and 9). Fusion 7 produced one stabilized cell line, but the Ab was not protective and was not saved. The RBF/Dn system did not produce any hybridomas, and reasons for this are not known.

TABLE 1

G6PDH Fusion Summary

| Fusion No. | Strain | Myeloma | Initial Positives | Stabilized Clones |
|---|---|---|---|---|
| 1 | Balb/c | 8.653 | 16 | 0 |
| 2 | Balb/c | 8.653 | 0 | 0 |
| 3 | Balb/c | 8.653 | 1 | 1 (+1 subclone) |
| 4 | Balb/c | 8.653 | 1 | 1 |
| 5 | Balb/c | 8.653 | 1 | 1 |
| 6 | Balb/c | 8.653 | 2 | 0 |
| 7 | Balb/c | 8.653 | 4 | 1 |
| 8 | CB6/F1 | 8.653 | 16 | 3 |
| 9 | Balb/c | 8.653 | 0 | 0 |
| 10 | CB6/F1 | 8.653 | 5 | 1 |
| 11 | CB6/F1 | 8.653 | 1 | 0 |
| 12 | RBF/Dn | HL-1 | 0 | 0 |
| 13 | RBF/Dn | HL-1 | 0 | 0 |

TABLE 2

G6PDH Clone Summary

| Clone | Subclass | Retained Enzyme Activity | Ascites |
|---|---|---|---|
| 3-2F8 | IgM, κ | No | ✓ |
| 3-2F8(e) [subclone of 3-2F8] | IgM | No | |
| 4-12C11 | IgM | No | ✓ |
| 5-12D7 | ND | No | |
| 8-10B3 | IgG$_1$, κ | Yes (77%)* | ✓ (81%)** |
| 8-10C7 | IgG$_1$, κ | Yes (80%)* | ✓ (80%)** |
| 8-12B4 | IgG$_1$, κ | Yes (78%)* | ✓ (84%)** |
| 10-4D6 | IgG$_1$, κ | Yes (87%)* | ✓ (85%)** |

*Percentages are the percent activity of QUN-G6PDH conjugate plus MAb after 10 min. at 40° C. vs. conjugate activity of a non-Ab containing control (which usually has between 45–50% of the activity of the control at RT). These figures are for supernatant Ab.
**These percentage enzyme activity figures are with ascites Ab.

3. Screening, Cloning, Characterization

The use of a secondary screen, the Thermal Protection Assay, after the primary ELISA, effectively narrowed the number of clones down to those which would protect the G6PDH from thermal stress. From the 13 fusions, eight hybridomas were stabilized (Table 1 summarizes all the fusions done), of which four showed enzyme protection (Table 2). With clone 8-10B3, 77–81% enzyme activity is retained as compared to only 45–50% enzyme activity with the non-Ab containing control, with 8-10C7 80% enzyme activity is retained, with 8-12B4 78–84% activity is retained, and with 10-4D6 85–87% activity is retained. Since these experiments only looked at one time point, 10 min., the percent activity retained may be even higher after a longer exposure to the higher temperature.

Example 2

Anti-G6PDH Antibodies that Stabilize G6PDH Conjugates without Inhibiting Enzyme Activity Various monoclonal anti-G6PDH antibodies prepared in a manner similar to that described above in Example 1 were tested to determine whether they would enhance the thermal stability of a quinidine-G6PDH conjugate utilized in the EMIT® quinidine assay sold by Syva Company. Complexes of various monoclonal anti-G6PDH antibodies with a quinidine-G6PDH conjugate were prepared as follows: Quinidine-G6PDH (~0.2 mg/ml) was mixed with a molar excess of antibody (~3 mg/ml). The mixture was incubated at 45° for 10' before measuring activity. A control sample was kept cold. Heating by itself at 45° C. for 10 minutes are conditions known to partially inactivate the enzyme. The results are summarized in Table 3 below. As can be seen III F2 and VIIF9 improved the stability of the enzyme markedly whereas the other antibodies stabilized the enzyme to a lesser degree.

TABLE 3

| Antibody | % Activity Lost at 45° |
|---|---|
| — | 82 |
| IIID1 | 66 |
| IIIE2 | 62 |
| V6A10 | 69 |
| VIIF9 | 39 |
| V4E1 | 50 |
| IIIF2 | 28 |
| VIIC10 | 76 |
| 1H9 (FAB fragment) | 84 |

Next, the effect of monoclonal Anti-G6PDH antibodies on the Extent of Inhibition of a Digoxin-G6PDH by Anti-Digoxin was determined.

Some of the monoclonal antibodies described above were studied, namely, VIIF9, IIIF2 and IIIE1. Complexes of these monoclonal anti-G6PDH antibodies with a digoxin-G6PDH conjugate were prepared. 150 ng of a digoxin-G6PDH conjugate was incubated with 5 µg of the indicated monoclonal antibody in 0.5 mL buffer for greater than 30 minutes. 50 µL of the indicated dilution of sheep anti-digoxin antiserum in 200 µL of buffer was then added, followed immediately by 250 µL of buffer containing enzyme substrates. The enzyme activity was determined at 37° by measuring the increase in absorbance at 340 nm over 30 sec. after a 15 sec. delay. The enzymatic activity of the complexes was determined in the presence of various dilutions of sheep anti-digoxin to see if there were any interactions between the two sets of antibodies. As can be seen in Table 4 below, the various monoclonal antibodies behaved differently. Antibody IIIE1 was highly inhibitory, IIIF2 was not significantly inhibitory, but diminished the extent of inhibition by anti-digoxin, and VIIF9 was non-inhibitory and had no effect on the inhibition by anti-digoxin. VIIF9, therefore, is a preferred antibody to stabilize G6PDH in a conjugate of G6PDH and digoxin for use in an assay for digoxin.

TABLE 4

| Monoclonal Anti-G6PDH | Enzymatic Activity (mOD/30s) Dilution of Anti-Digoxin | | | | % Inhibition by Anti-G6PDH | % Inhibition by Dilution of Anti-Digoxin | | |
|---|---|---|---|---|---|---|---|---|
|  | 1/3200 | 1/3200 | 1/800 | 1/200 |  | 1/3200 | 1/800 | 1/200 |
| None | 213 | 204 | 174 | 104 | — |  | 18 | 51 |
| VIIF9 | 220 | 211 | 183 | 109 | (3) | 4 | 17 | 50 |
| IIIF2 | 205 | 196 | 173 | 110 | 4 | 4 | 16 | 46 |
| IIIE1 | 26 | 26 | 20 | 14 | 88 | 0 | 23 | 45 |

Example 3

Stabilization of HRP utilizing Anti-HRP

Native horseradish peroxidase (HRP) was diluted to 1 µg/ml in 0.1M $NaH_2PO_4$/0.2M NaCl containing 2 g/l bovine gamma globulins (Miles Labs, labile enzyme free). Ascites containing monoclonal antiHRP (from cell line HRP-PEN 8G9 prepared in a manner similar to that described in Example 1) was added to aliquots of the enzyme solution (10 µl ascites per ml enzyme solution). After equilibration for 1 hour at 22° C., the aliquots were placed in a 65° C. water to determine kinetics of thermal inactivation. At various times, aliquots were removed to an ice bath to halt the inactivation. HRP activity of each aliquot was subsequently determined.

Under these experimental conditions, HRP in the absence of antibody to HRP showed a half life at 65° C. of 56 minutes; in the presence of antibody, the half life was estimated to be 214 minutes at 65° C.

To demonstrate that anti-HRP is compatible with an assay, the following experiment was conducted. Theophylline enzyme reagent (clinical lot X01 for Syva Company, 0.4 mg/l HRP-Theophylline in 0.1M $NaH_2PO_4$/0.2M NaCl, containing 2 g/l bovine gamma globulins, 100 mg/l Glucose Oxidase, plus detergent and stabilizers) was supplemented with anti-HRP ascites (from cell line 8G9, 10 µl ascites per ml enzyme reagent) and used to run a theophylline calibration curve for Syva Company's Acculevel® assay protocol. Strips had anti-theophylline MAb immobilized on them. Untreated enzyme reagent was also run as a control.

The calibration curves were virtually identical in terms of color bar heights. There was some evidence that the effective affinity of binding between the anti-theophylline and the HRP-theophylline was slightly reduced in the presence of the anti-HRP; the manifestation of this was slightly more diffuse color fronts.

Example 4

EMIT® assay using anti-G6PDH

MAbS 8-10B3, 8-10C7, 8-12B4, and 10-4D6, which were prepared in Example 1 and showed a protective effect were further tested for their effect in EMIT® assays. MAbs were spiked into the Theophylline and Quinidine EMIT® Assays (Syva Company, Palo Alto, Calif.).

A. EMIT Assay Protocol

Stasar set-up:
Concentration mode, 340 nm, 30° C. Set Times mode, 15-sec. delay, 30-sec. read Assay: EMIT kit reagents were used.

(a) Fifty µL of Reagent B plus 50 µL of diluted ascites Ab (1:10 in assay buffer) or buffer as a control, plus 200 µL of assay buffer were placed into a Crohn cup using a Pipetman. The cups were incubated 10 min. at RT. One cup was made for every calibrator or sample run in the assay (i.e., seven calibrators means seven cups of each Mab).

(b) Fifty µL of each calibrator or other sample plus 250 µL of assay buffer were placed in another cup using the pipetter-diluter.

(c) Fifty µL from step b plus 250 µL of assay buffer were placed into an assay cup using the pipetter-diluter.

(d) Fifty µL of Reagent A plus 250 µL of assay buffer were added to the assay cup using the pipetter-diluter. This addition was made as the Stasar was purging the flow cell.

(e) Using a Pipetman, 300 µL from the step a cup were added to the assay cup, and the mixture was read on the Stasar.

(f) The process was repeated with all calibrators or samples for each ascites Ab and buffer control.

(g) The $\Delta A-\Delta A_o$ for each calibrator was calculated, along with the change in separations between different calibrators (e.g., Neg to 0.5), and the values given with the MAbs were compared to those with the buffer controls. If the Ab did not interfere in the assay, the values should be equivalent.

Various calibrator concentrations were used (for THP: Neg, 2.5, 5, 10, 20, and 40 µg/mL; for QUN: Neg, 0.5, 1, 2, 4, and 8 µg/mL) with and without the anti-G6PDH MAb (50 µL 1:10 ascites Ab) in Reagent B.

B. Results

The effect of adding the four MAbs to either the QUN or THP EMIT assays was determined. The absorbance readings obtained when the EMIT assay standard curve was run in the presence of protective MAb or buffer control were determined. For the THP EMIT assay, the presence of 8-10B3, 8-10C7, and 8-12B4 did not alter the results given by the calibrators; the curves were parallel and nearly superimposed. For 10-4D6, the presence of the MAb appeared to give a signal improvement in the standard curve, with slightly higher absorbance readings and a slightly steeper slope of the curve.

The effect of the MAbs on the QUN EMIT standard curve were slightly different. For 8-10C7 and 8-12B4, the curves were again nearly identical. With 8-10B3, there appeared to be a decrease in separations at the upper end of the curve, as shown by a leveling off of the slope of the curve. MAb 10-4D6 gave a parallel curve to the curve given with buffer; however, the absorbance readings for the calibrators are all slightly higher with this MAb. Both with supernatant and ascites MAb, 10-4D6 showed the greatest percent protection of enzyme activity, 85–87%, of the four MAbs.

Example 5

Cyclosporin EMIT® Assay

Details of the EMIT® Assay protocol are described in U.S. Pat. No. 3,817,837 (1974). An antibody capable of recognizing cyclosporin A was prepared by routine hybridoma techniques using a mixture of cyclosporin A conjugated, through a glycylglycine extended paracarboxybenzyl linking group, at the alanine nitrogen atoms of cyclosporin A amino acid residues No. 7 and 8 to keyhole limpet hemocyanin, and is, for this Example, referred to as anti-CsA monoclonal antibody. A G6PDH-cyclosporin A conjugate comprising cyclosporin A conjugated, through an acetocarbamate extended hydroxyethyl linking group, at the alanine nitrogen atom of cyclosporin A amino acid residue No. 7 to glucose-6-phosphate dehydrogenase, was prepared and is, for this Example, referred to as a CsA-G6PDH conjugate. An antibody capable of recognizing cyclosporin A metabolite M1 (Maurer, G. *Drug Metabolism and Disposition* 1984, 12(1), 120–6) but substantially incapable of recognizing cyclosporin A or the G6PDH-cyclosporin A conjugate was prepared by routine hybridoma techniques using an atiocyclosporin carboxaldehyde (prepared by ozone/dimethylsulfide cleavage of M1) conjugated, through an oxyacetic acid imino linking group, to keyhole limpet hemocyanin and is, for this Example, referred to as an anti-M1 antibody. The assay was performed on the COBAS MIRA analyzer.

One hundred microliters of a whole blood sample and 6 calibrators were separately vortexed with 200 µL methanol. The methanol lysed the cells, solubilizes the cyclosporin A, and precipitates most of the blood proteins. After a one-minute incubation, the mixture was centrifuged. The supernatant was diluted 1 to 3 with pretreatment diluent. On the analyzer, 36 µL of the resulting pretreated sample was incubated for 75 seconds with 155 µL of the monoclonal anti-CsA antibody reagent, which includes substrate and cofactor. Subsequently, 75 µL of the CsA-G6PDH conjugate reagent was added. After a 175 second incubation, enzyme activity, which is a function of drug concentration, was monitored by following the production of NADH spectrophotometrically at 340 run for 100 seconds.

The monoclonal anti-CsA antibody reagent contained the monocolonal anti-CsA antibody, nicotinamide adenine dinucleotide, glucose-6-phosphate, anti-M1 antibody (included for measurement of metabolite cross-reactivity), sodium chloride, bulking agent, surfactant, and preservatives.

The CsA-G6PDH conjugate reagent contained the enzyme conjugate, tris buffer, bulking agents, stabilizers, and preservatives.

The diluent contained tris buffer, surfactant, and preservatives.

Each of the reagents was formulated to be consistent with standard EMIT technology. Bulking agents, surfactants and preservatives were selected, which allow for ease of use and storage of the reagents.

The CsA-G6PDH conjugate reagent was stabilized with an antibody for glucose-6-phosphate dehydrogenase (4D6), which antibody was prepared as described in Example 1. The anti-G6PDH antibody was used as a stabilizer for the CsA-G6PDH conjugate reagents.

Twenty samples and six calibrators were pretreated and assayed under this protocol in less than two hours.

The assay standard curve range extended to 500 ng/mL. Analytical recovery within the curve range varied from 95 to 104%. Within run precision with trilevel controls ranged from 5.0 to 7.1% CV. Between run precision with the same controls ranged from 4.9 to 7.4% CV. The results are summarized in Table 5.

TABLE 5

| ASSAY PARAMETERS ON COBAS MIRA ANALYZER | |
|---|---|
| Assay Temperature | 37° C. |
| Wavelength | 340 nm |
| Volume of Pretreated Sample | 36 µL |
| Diluent Volume (water) | 59 µL |
| Antibody Reagent Volume | 155 µL |
| Incubation Time (sample + antibody reagent) | 75 sec |
| Enzyme Reagent Volume | 75 µL |
| Delay Time (sample + antibody and enzyme reagents) | 175 sec |
| Read Time | 100 sec |

Three levels of cyclosporin A were spiked into 10 fresh cyclosporin A-negative whole blood samples. The samples were assayed in duplicate. The results are summarized in Table 6.

TABLE 6

| SPIKED CONC. (ng/mL) | 75 | 250 | 400 |
|---|---|---|---|
| N | 10 | 10 | 10 |
| Mean (ng/mL) | 74.3 | 237.1 | 396.7 |
| SD (ng/mL) | 6.2 | 11.8 | 18.0 |
| CV (%) | 8.4 | 5.0 | 4.5 |
| Recovery (%) | 99.0 | 94.8 | 99.2 |

Five levels of cyclosporin A were spiked into two discrete samples of fresh cyclosporin A-negative whole blood. The samples were assayed in duplicate. The results are summarized in Table 7.

TABLE 7

| SPIKED CONC. (ng/mL) | 35 | 75 | 150 | 275 | 425 |
|---|---|---|---|---|---|
| N | 2 | 2 | 2 | 2 | 2 |
| Mean (ng/mL) | 41.6 | 77.8 | 151.6 | 277.6 | 420.4 |
| Recovery (%) | 118.8 | 103.7 | 101.1 | 100.9 | 98.9 |

Within-run precision was performed on 20 distinct sample extracts at each of three levels. Between-run precision was performed at each of three levels in a total of 20 runs on two analyzers. Distinct sample extracts were assayed in each run, and quantitations were from concurrent standard curves. The results are summarized in Table 8.

TABLE 8

|  | N | Mean (ng/mL) | SD (ng/mL) | CV (%) |
|---|---|---|---|---|
| Within-run | 20 | 82.3 | 5.6 | 6.8 |
|  | 20 | 187.3 | 9.4 | 5.0 |
|  | 20 | 372.2 | 26.4 | 7.1 |
| Between-run | 20 | 91.1 | 6.7 | 7.4 |
|  | 20 | 183.9 | 9.0 | 4.9 |
|  | 20 | 356.6 | 17.5 | 4.9 |

Example 6

Stabilization of Phenobarbital-G6PDH Conjugate and Assay

A phenobarbital-G6PDH conjugate (utilized in the EMIT phenobarbital assay sold by Syva Company) was stored at 30° C. in either an aqueous buffered medium contained bulking agents and preservatives, or the same medium, but containing monoclonal anti-G6PDH 10C7 prepared as described in Example 1. The enzyme activity was measured at various times and the results are summarized in Table 9.

TABLE 9

| Time at 30° C. | % Activity Loss | |
|---|---|---|
| | Conjugate | Conjugate + 10C7 |
| 0 days | 0 | 0 |
| 4 days | 7 | 1 |
| 28 days | 16 | 5 |

An assay was carried out for phenobarbital in a manner analogous to that used for the assay of cyclosporin described in Example 5, except that the samples used were serum containing various amounts of phenobarbital. The assay was performed using either the conjugate or the conjugate mixed with monoclonal anti-G6PDH. The increase in enzyme rate in the presence of analyte above that observed in the absence (R-Ro) was ascertained and appears in Table 10.

TABLE 10

Standard Curve for Phenobarbital (R—Ro)

| Phenobarbital Concentration (ug/mL) | Conjugate | Conjugate + 10C7 |
|---|---|---|
| 0 | 0 | 0 |
| 5 | 3.0 | 2.4 |
| 10 | 4.2 | 3.3 |
| 20 | 5.3 | 4.8 |
| 40 | 7.0 | 6.5 |
| 80 | 8.5 | 8.3 |

Example 7

Stabilization of Carbamazepine-G6PDH Conjugate and Assay

A carbamazepine-G6PDH conjugate (utilized in the EMIT carbamazipine assay sold by Syva Company) was stored at 30° C. in either an aqueous buffered medium containing bulking agents and preservatives, or the same medium, but also containing monoclonal anti-G6PDH 4D6 prepared as described in Example 1. The enzyme activity was measured at various times and is summarized in Table 11.

TABLE 11

| Time at 30° C. | % Activity Loss | |
|---|---|---|
| | Conjugate | Conjugate + 10C7 |
| 0 days | 0 | 0 |
| 4 days | 26 | 7 |
| 28 days | 50 | 19 |

An assay was carried out for phenobarbital in a manner analogous to that used for the assay of cyclosporin as described in Example 5, except that the samples used were serum containing various amounts of phenobarbital. The assay was performed using either the conjugate or the conjugate mixed with anti-G6PDH 4D6. The increase in enzyme rate in the presence of analyte above that observed in the absence of analyte (R-Ro) was ascertained and appears in Table 12.

TABLE 12

Standard Curve for Phenobarbital (R—Ro)

| Phenobarbital Concentration (ug/mL) | Conjugate | Conjugate + 10C7 |
|---|---|---|
| 0 | 0 | 0 |
| 2 | 6.3 | 5.9 |
| 4 | 11.6 | 9.5 |
| 8 | 15.2 | 13.7 |
| 12 | 18.1 | 16.0 |
| 20 | 20.8 | 18.9 |

Although the foregoing invention has been described in some detail by way of illustration and example for the purposes of clarity and understanding, it will be obvious that certain changes or modifications may be practiced within the scope of the appended claims.

What is claimed is:

1. A method for stabilizing a conjugate of an enzyme and a member of a specific binding pair having a molecular weight of 100 to 2000 (enzyme conjugate), said method comprising the step of combining said enzyme conjugate with an antibody for said enzyme wherein said antibody is employed in a molar amount that is 5-fold or greater than the molar amount of said enzyme conjugate, said amount being sufficient to bind at least 90% of said enzyme conjugate, and wherein said antibody is capable of stabilizing said enzyme in said enzyme conjugate against thermal inactivation and does not substantially inhibit the activity of said enzyme and does not substantially inhibit the ability of said enzyme conjugate to bind to an sbp member complementary to said member.

2. The method of claim 1 wherein said enzyme is a dehydrogenase.

3. The method of claim 1 wherein said enzyme is a glucose-6-phosphate dehydrogenase.

4. The method of claim 1 wherein the enzyme is a malate dehydrogenase.

5. The method of claim 1 wherein said enzyme is a peroxidase.

6. The method of claim 1 wherein said enzyme is horseradish peroxidase.

7. The method of claim 1 where said enzyme is glucose oxidase.

8. The method of claim 1 wherein said member is a hapten.

9. The method of claim 1 wherein said antibody for said enzyme is a monoclonal antibody.

10. In an assay for an analyte having a molecular weight of 100 to 2000, said assay comprising the steps of (a) combining a medium suspected of containing said analyte with a reagent that is a conjugate of an enzyme and a first member of a specific binding pair (sbp) that is an analyte analog and with a second member of a specific binding pair complementary to said first member wherein the enzyme activity of said enzyme is modified upon the binding of said second sbp member to said first sbp member in said conjugate, and (b) determining the enzyme activity of said enzyme by reacting said enzyme with a substrate for said enzyme as an indication of the presence or amount of said analyte, the improvement comprising employing as said reagent said conjugate and an antibody for said enzyme, which antibody is capable of stabilizing said enzyme in said conjugate against thermal inactivation, does not substantially inhibit the activity of said enzyme, and does not substantially inhibit the ability of the first sbp member to bind to said second sbp member, wherein said antibody is employed in a molar amount that is 5-fold or greater than the molar amount of said enzyme conjugate, said amount being sufficient to bind at least 90% of said enzyme conjugate.

11. The method of claim 10 wherein said enzyme is a dehydrogenase.

12. The method of claim 10 wherein said enzyme is a glucose-6-phosphate dehydrogenase.

13. The method of claim 10 wherein said enzyme is malate dehydrogenase.

14. The method of claim 10 wherein said enzyme is horseradish peroxidase.

15. The method of claim 10 wherein said enzyme is glucose oxidase.

16. The method of claim 10 wherein said first sbp member is a hapten.

17. The method of claim 10 wherein said antibody for said enzyme is a monoclonal antibody.

18. A method of determining an analyte having a molecular weight of 100 to 2000 comprising the steps of:
(a) providing in combination (1) a medium suspected of containing said analyte, (2) a conjugate comprising an enzyme and an analyte analog, (3) an antibody for said enzyme which antibody is capable of stabilizing said enzyme in said conjugate against thermal inactivation, does not substantially inhibit the activity of said enzyme and does not substantially inhibit the ability of said analyte analog to bind to an antibody for said analyte, said antibody for said enzyme being employed in a molar amount that is 5-fold or greater than the molar amount of said conjugate, said amount being sufficient to bind at least 90% of said enzyme conjugate and (4) an antibody for said analyte, which binds to said conjugate and changes the activity of said enzyme, and
(b) determining the enzyme activity of said enzyme, the enzyme activity being related to the presence or amount of said analyte in said medium.

19. The method of claim 18 wherein said enzyme is a dehydrogenase.

20. The method of claim 18 wherein said enzyme is a glucose-6-phosphate dehydrogenase.

21. The method of claim 18 wherein said enzyme is malate dehydrogenase.

22. The method of claim 18 wherein said enzyme is horseradish peroxidase.

23. The method of claim 18 wherein said analyte is a drug of abuse.

24. The method of claim 18 wherein said analyte is a therapeutic drug.

25. The method of claim 18 wherein said antibody for said enzyme is a monoclonal antibody.

26. The method of claim 18 wherein said items (2) and (3) are provided as a preformed immune complex.

27. The method of claim 18 wherein said combination comprises a substrate for said enzyme.

28. A composition comprising (1) a conjugate of an enzyme and a member of a specific binding pair (sbp) having a molecular weight of 100 to 2000 and (2) an antibody for said enzyme, which antibody is capable of stabilizing the enzyme in said conjugate against thermal inactivation and does not substantially inhibit the activity of said enzyme and does not substantially inhibit the ability of the sbp member of said conjugate to bind to its complementary sbp member, wherein said antibody is present in said composition in a molar amount that is 5-fold or greater than the molar amount of said conjugate, said amount being sufficient to bind at least 90% of said enzyme conjugate.

29. The composition of claim 28 wherein said enzyme is a dehydrogenase.

30. The composition of claim 28 wherein said enzyme is a glucose-6-phosphate dehydrogenase.

31. The composition of claim 28 wherein said enzyme is malate dehydrogenase.

32. The composition of claim 28 wherein said enzyme is horseradish peroxidase.

33. The composition of claim 28 wherein said enzyme is glucose oxidase.

34. The composition of claim 28 wherein said member is a hapten.

35. The composition of claim 28 wherein said antibody for said enzyme is a monoclonal antibody.

36. A kit comprising in packaged combination (a) composition comprised of (1) a conjugate of an enzyme and a member of a specific binding pair (sbp) having a molecular weight of 100 to 2000 and (2) an antibody for said enzyme, which antibody is capable of stabilizing said enzyme in said conjugate and does not substantially inhibit the activity of said enzyme and does not substantially inhibit the ability of said member to bind to its complementary sbp member, wherein said antibody is present in said composition in a molar amount that is 5-fold or greater than the molar amount of said conjugate, said amount being sufficient to bind at least 90% of said enzyme conjugate, and (b) a substrate for said enzyme.

37. The kit if claim 36 wherein said enzyme is a dehydrogenase.

38. The kit of claim 36 wherein said enzyme is glucose-6-phosphate dehydrogenase.

39. The kit of claim 36 wherein said enzyme is malate dehydrogenase.

40. The kit of claim 36 wherein said enzyme is horseradish peroxidase.

41. The kit of claim 36 wherein said enzyme is glucose oxidase.

42. The kit of claim 36 wherein said member is a hapten.

43. The kit of claim 36 wherein said antibody for said enzyme is a monoclonal antibody.

44. The kit of claim 36 further comprising an antibody for said member.

* * * * *